United States Patent [19]

Gibbs

[11] Patent Number: 4,946,672
[45] Date of Patent: Aug. 7, 1990

[54] DEODORIZING COMPOSITIONS

[75] Inventor: Anthony Gibbs, Norwich, United Kingdom

[73] Assignee: Walex Products Company, Jamestown, N.C.

[21] Appl. No.: 275,431

[22] Filed: Nov. 22, 1988

Related U.S. Application Data

[63] Continuation-in-part of Ser. No. 70,911, Jul. 8, 1987, Pat. No. 4,818,524.

[30] Foreign Application Priority Data

Jul. 9, 1986 [GB] United Kingdom ................ 8616740
Dec. 5, 1986 [GB] United Kingdom ................ 8629179

[51] Int. Cl.$^5$ ............................................. A61L 9/01
[52] U.S. Cl. ............................... 424/76.1; 424/76.21; 424/76.5; 424/76.6; 424/76.8; 435/262; 435/264; 528/422
[58] Field of Search ............ 528/422; 424/76.1, 76.8; 435/262, 264

[56] References Cited

U.S. PATENT DOCUMENTS 2,325,586 8/1943 Bolton et al. ................. 528/422
2,336,605 12/1943 Ernsberger et al. ............ 528/422
4,818,524 4/1989 Gibbs .

Primary Examiner—Sam Rosen
Attorney, Agent, or Firm—Ostrolenk, Faber, Gerb & Soffen

[57] ABSTRACT

The invention provides an odor removal composition characterized by:

(a) a complexing agent selected from a biguanide polymer of the formula (1)

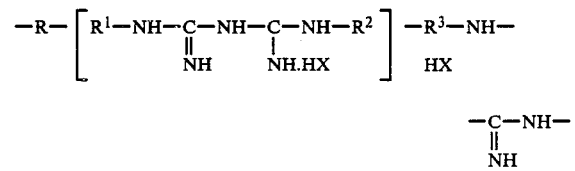

in which R, $R^2$, $R^2$ and $R^3$ are each a substituted or unsubstituted alkylene group having up to 12 carbon atoms in the main chain, HX is an acid; and n has a value of 2 to 20.

(b) a carrier capable of assisting wetting of odor forming compositions; and (c) a cationic moiety; said moiety being part of a chemically independent compound, or chemically associated with a complexing agent or the carrier.

15 Claims, No Drawings

DEODORIZING COMPOSITIONS

This is a continuation-in-part of application Ser. No. 070,911 filed July 8, 1987, now U.S. Pat. No. 4,818,524.

DESCRIPTION

This invention relates to deodourising compositions. Present technology in connection with odour control has generally been in the field of masking odours rather than actually removing them.

The present invention seeks in a first aspect to provide a broad spectrum deodourising composition.

According to a first aspect therefore of the present invention there is provided an odour removing composition characterised by:

(a) a complexing agent selected from a Biguanide polymer of the formula (1):

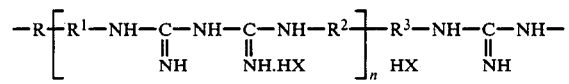

in which R, $R^1$ $R^2$ and $R^3$ are each a substituted or unsubstituted alkylene group having up to 12 carbon atoms in the main chain, HX is an acid; and n has a value of 2 to 20;

(b) a carrier capable of assisting wetting of odour forming compositions; and (c) a cationic moiety; said moiety being part of a chemically independent compound, or chemically associated with the complexing agent or the carrier.

Although most compositions can be deodourized using the invention the compositions are less effective on substances such as kerosene for example. The invention is most effective on organic compounds containing hetero atoms, particularly organically bound N and S.

The acid HX is preferably an inorganic acid, most preferably sulphuric or hydrochloric acid. The composition may additionally comprise an auxiliary complexing agent. Suitable complexing agents for use in the inventive compositions as hereinbefore set forth may be salts of transition metals, for example the products of a reaction of copper with an organic acid such as lactic, citric, or ascorbic acids.

The deodorising compositions of the invention may thus comprise a complexing agent selected from one or more salts of an organic acid and a transition metal ion capable of oxidation; a carrier capable of assisting wetting of odour forming compositions, and a cationic moiety; said moiety being part of a chemically independent compound, or chemically associated with the carrier or complexing agent.

The compositions of the present invention include an effective amount of a wetting agent as a carrier, which may be cationic and serve as the cationic agent as well. Alternatively, the wetting agent may a non-ionic or amphoteric detergent carrier, to assist in establishing contact between the active ingredients of the composition of the invention and the article or surface to be deodourised. The compositions of the present invention may in certain circumstances be incorporated within an article such, for example, a foam or sponge plastic of a textile material or the like to provide a more permanent deodourising action.

In a further embodiment of the present invention the composition additionally comprises a substantially odourless liquid carrier of low volatility, said carrier either acting in synergism with the composition or at least being chemically inert relative thereto. The liquid carrier acts to retain the deodourizing compositions in reaction solution even when higher volatility carriers such as water have evaporated. Thus the liquid carriers are particularly suitable to hot climates.

The liquid carriers may be selected from substantially odourless aromatic esters, for example ethylene, diethylene or polyethylene glycols, fatty acid esters, dimethylformamate, DMA, lactones and pyrrolidones. These substituents when added to the deodourising compositions in accordance with the present invention including water for example prolong the reactive life of the system and hence provide better odour utilizing qualities.

In order to maintain in the formulation pH values providing adequate shelf life and a high level of activity and also to prevent excessive changes of the pH when the formulation comes into contact with acidic or alkaline media, a buffering agent may be added to adjust to and maintain a suitable pH range.

The pH of the concentrated formulation should be between 3 and 12, preferably between 5.5 and 10.

Further, betain compounds may be added to the composition of the present invention; these provide synergistic odour removal compositions. It is a feature of the invention that at least one of the active components may be present as an acid or salt of low solubility in an aqueous media to give slow release properties to the composition.

The precise mechanism whereby the composition in accordance with the present invention operates is not presently understood, but it is thought that the composition seeks to decompose or "attack" the odour forming constituent rather than simply mask the odour. It may do this by forming a complex with the odour forming compositions which reduces volatility, or odour forming abilities, or by chemically interacting with, and thus removing odour forming capability of the odour emitting components.

In a further embodiment of the invention the composition may include an effective amount of selected enzymes capable of degrading odour-emitting compounds.

The composition in accordance with the present invention may be provided in a liquid gel or powder form. When provided in a powder form the constituents of the composition are preferably adsorbed in a carrier powder. A typical carrier powder in accordance with the present invention comprises sodium carbonate and sodium triphosphate; a cross-linked polyacrylamide, pumice dust, or keiselghur. For many applications the incorporation of the composition into a slow release system has been found a very convenient method for achieving longer term odour elimination. Such slow release systems may comprise a matrix material (which may be porous to increase surface area) into which the composition is incorporated, a receptacle with at least one wall through which the composition will diffuse, or addicts or salts of at least one component of the composition which have reduced solubility so that the rate of release is to the desired level.

Another form of carrier for the active biguanide compound may be selected from an aromatic ester for example an alkylene glycol, fatty acid ester dimethylformamate lactones or pyrrolidones. These may be added in minor amounts to the aqueous compositions of the invention to retain the active biguanide composition in reactive juxtaposition with a target odour former.

In a typical embodiment of the first aspect of the present invention, the composition comprises 20% to 80% by volume of the quaternary ammonium compound and 5% to 40% by volume of the polymer of formula (1) and up to 75% by volume of wetting agent. In the second aspect of the present invention the composition generally comprises up to 10 parts by volume of the quaternary ammonium salt, although higher proportions of up to 50% are possible. The carrier may comprise up to 40 parts by volume while the complexing agent which is present at 100 parts by volume. The composition may be diluted by up to 500% by volume of water. This produces a concentrate which maybe subsequently further diluted prior to use. The extent of dilution will depend on the circumstances and particular application of the composition in accordance with the present invention.

The quaternary ammonium compound is preferably a substituted or unsubstituted aromatic quaternary ammonium salt and is typically a substituted benzyl quaternary ammonium salt. In a specific embodiment of the invention the quaternary ammonium salt is dimethyl benzyl ammonium chloride.

The polymer is preferably a polymeric biguanide having the general formula:

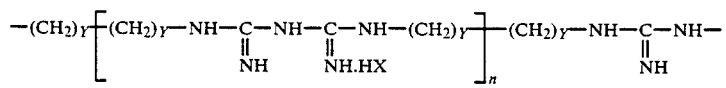

wherein Y is 3 and n is 5 to 15, and HX is an inorganic acid.

The wetting agent may be a cationic surfactant or a nonionic surfactant. Where the wetting agent is a nonionic surfactant it preferably has a Hydrophobic-Lipophilic balance (H.L.B.) within the range of 12 to 16 and preferably within the range of 13 to 15. A typical nonionic surfactant for use in accordance with the present invention is nonyl phenol ethylene oxide although it will be appreciated by the man skilled in the art that other surfactants of similar properties may be employed.

The compositions in accordance with the present invention have also been found to have disinfecting properties, especially when used in addition to other known disinfecting agents. The composition also have fungistatic and even fungicidal properties and are also thought to effective against, for example, athlete's foot infections around swimming pools, changing rooms and sports areas.

In a powder of spray form they can keep odour under control in sports footwear, while at the same time will reduce the possibility of infection from microorganisms which may develop in such footwear.

The compositions are effective in clinics, hospitals, homes for the aged and other areas where odour control is required, for example, in the case of incontinency problems.

The compositions may be sprayed onto furniture, upholstery fabrics, slippers, clothing or carpets all to prevent odour. In the latter application to carpets, control has been particularly effective where pets or babies are known to cause odour problems.

Furthermore, the compositions may be employed in restaurants, hospitals or schools; for wiping tables, furniture rails etc., to remove odour and to inhibit the growth of microorganisms.

Where a cationic surfactant is employed, the compositions have antistatic properties as well as odour control effects which makes them useful for inhibiting the build up of static electricity. The compositions can be introduced into foams and sponges. They are also used for the control of fish smells, toilet odours and control of damp and mould and bilge odours in boats.

Compositions formulated in accordance with the present invention have a long shelf life and are stable at ambient temperatures. The compositions tends to form water insoluble precipitates with anionic surfactants, soaps strong alkalis and complex phosphates.

The formulation in accordance with the present invention is readily soluble in hot, cold, fresh or salt water and a high degree of hardness has little, if any, depressant effect on the odour control ability.

Following is a description by way of example only of methods of carrying the invention into effect.

EXAMPLE 1

A liquid formulation in accordance with the present invention was prepared as follows:

Dimethyl Benzyl Ammonium Chloride or 60% concentrates -35 liters

Polymeric Biguanide having the general chemical structure:

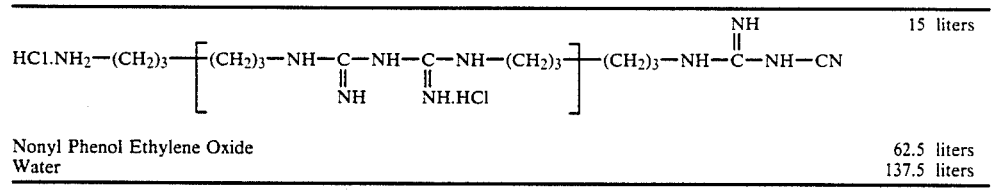

| | |
|---|---|
| Nonyl Phenol Ethylene Oxide | 62.5 liters |
| Water | 137.5 liters |

The required volume of the quaternary ammonium compound, biguanide and surfactant are added to the tank and the required quantity of any marking dye is also added. The total volume is then made up to a total of 250 liters with filtered mains water. The liquid thus formed is stirred until uniform and the resultant liquid composition represents a concentration of approximately 10 times normal use strength.

The composition is then diluted to normal strength and then packed with instruction for use.

EXAMPLE 2

A composition was prepared as follows:

| | |
|---|---|
| Dimethyl Benzyl Ammonium Chloride | 17.5 liters |
| Polymeric Biguanide having the general formula as set forth in Example 1 | 7.5 liters |
| Nonyl Phenol Ethylene Oxide | 31.25 liters |

The constituents were introduced into a tank of capacity of 250 liters, a small quantity of dye was added and water (193.75 liters) was then added to bring the volume up to 250 liters.

20 liters of this composition were added to 40 Kg of sodium carbonate and 20 Kg of sodium tripolyphosphate.

The solid ingredients were introduced into a mixer and the liquid composition was slowly added while mixing. On completion of the introduction of the liquid composition the mixing was carried out for a further 60 minutes and then allowed to cool before passing through a vibrating sieve.

The composition has to be kept under dry conditions.

It has been found that the liquid composition of Example 1 and the powder composition of Example 2 are extremely effective in eliminating odours. The powder composition produced in Example 2 is readily soluble in water, either hot or cold for direct application to an area in which an odour is to be eliminated.

EXAMPLE 3

Various odour-neutralising formulations are shown in Table A, hereinafter set forth. These formulations include a first component formed as follows:
Polymeric biguanide
Quaternary Ammonium Compound (Dimethyl Benzyl Ammonium Chloride)
Non-ionic surfactant
Water Depending upon the final product requirement the ratio of Polymer to quaternary compound to surfactant can range, typically, as follows:

| Basic Formulation | Polymer | Quaternary | Surfactant |
|---|---|---|---|
| (A) Low detergency/low foam | 5 | 20 | 0 |
| (B) Medium detergency/low foam | 5 | 40 | 2 |
| (C) High detergency/medium foam | 5 | 40 | 40 |

All formulations are by volume.

Various formulations are shown in Table 1 which use the above formulations plus other chemicals as noted.

TABLE 1

1. LOW FOAM GLASS WASH

| | |
|---|---|
| Basic formulation (A) | 20% |
| Sodium Hydroxide (40%) | 2% |
| Non-ionic Surfactant | 2% |
| Water to 100% | |

2. DEODORIZING WAX POLISH

| | |
|---|---|
| Basic formulation (A) | 10% |
| Fatty carnauba Wax | 60% |
| Non-ionic Surfactant | 10% |
| Water to 100% | |

3. TOILET FLUID

| | |
|---|---|
| Basic formulation (A) | 10% |
| Formaldehyde | 10% |
| Non-ionic surfactant | 5% |
| Water to 100% | |

4. TOILET FLUID (PERFUMED)

| | |
|---|---|
| Basic formulation (A) | 40% |
| Isopropyl alcohol | 10% |
| Perfume | 2% |
| Water to 100% | |

TABLE 1-continued

5. HIGH TEMPERATURE HIGH PRESSURE SURGICAL INSTRUMENT WASH

| | |
|---|---|
| Basic formulation (A) | 20% |
| Non-ionic Surfactant | 20% |
| Sodium Hydroxide | 2% |
| Anti-foam | As required |
| Water to 100% | |

6. ULTRASONIC CLEANING FLUID

| | |
|---|---|
| Basic formulation (A) | 10% |
| Non-ionic Surfactant | 20% |
| Sodium Hydroxide | 2% |
| Water to 100% | |

7. HIGH PRESSURE WASH FOR SHIPPING CONTAINER

| | |
|---|---|
| Basic formulation (A) | 40% |
| Formaldehyde | 2% |
| Non-ionic Surfactant | 10% |
| Water to 100% | |

8. TOILET BOWL STAIN REMOVER

| | |
|---|---|
| Basic formulation (B) | 10% |
| Hydrochloric Acid | 9% |
| Non-ionic Surfactant | 5% |
| Water to 100% | |

9. BEER LINE AND PUMP CLEANER

| | |
|---|---|
| Basic formulation (B) | 10% |
| Sodium Hydroxide | 12% |
| Non-ionic Surfactant | 10% |
| Water to 100% | |

10. GLASS LIQUOR DISPENSER CLEANER

| | |
|---|---|
| Basic formulation (B) | 5% |
| Non-ionic Surfactant | 10% |
| Sodium Hydroxide | 5% |
| Water to 100% | |

11. HARD SURFACE CLEANER

| | |
|---|---|
| Basic formulation (C) | 60% |
| Sodium Hydroxide | 2% |
| Water to 100% | |

12. HAND GLASS WASH FLUID

| | |
|---|---|
| Basic formulation (C) | 20% |
| Non-ionic Surfactant | 20% |
| Water to 100% | |

13. JANITORIAL DETERGENT

| | |
|---|---|
| Basic formulation (C) | 40% |
| Non-ionic Surfactant | 20% |
| Water to 100% | |

14. PRE-SOAK CLEANING FLUID

| | |
|---|---|
| Basic formulation (C) | 20% |
| Sodium Hydroxide | 5% |
| Non-ionic Surfactant | 10% |
| Water to 100% | |

BASIC FORMULATION (D) / EXAMPLE 4

| Components | |
|---|---|
| Polymeric Biguanide (20% conc) | 5% |
| Quaternary Ammonium Compound (60% conc) | 20% |
| Non-ionic surfactant (80% conc) | 20% |
| Citric acid (1 mole solution) | 1% |
| Ferrous Sulphate (1 mole solution) | 10% |
| Water to | 100% |

All % are by volume.

TABLE 2

1. GLASS WASH

| | |
|---|---|
| Basic formulation (D) | 10% |
| Non-ionic Surfactant | 3% |
| Water to 100% | |

2. UPHOLSTERY CLEANER

| | |
|---|---|
| Basic formulation (D) | 20% |
| Non-ionic Surfactant | 20% |
| Isopropyl Alcohol | 5% |
| Water to 100% | |

TABLE 2-continued

| 3. CARPET STAIN REMOVER | |
|---|---|
| Basic formulation (D) | 50% |
| Citric acid (10 mole) | 15% |
| Water to 100% | |
| 4. PLASTIC CLEANER | |
| Basic formulation (D) | 20% |
| Non-ionic surfactant | 10% |
| Citric acid (10 mole) | 10% |
| Anti-foam | As required |
| Water to 100% | |

EXAMPLE 5

An odour elimination concentrate was prepared as follows:

| | |
|---|---|
| Polymeric biguanide | 2% |
| Quaternary ammonium compound (dimethyl benzylammoniumchloride) | 2% |
| Ascorbic acid | 5% |
| Ferrous sulphate | 0.1 mole on molar concentration of absorbic acid |
| Water to (pH adjusted to 6.5) | 100% |

A diluted solution of this formulation (1 part of solution in 25 parts of water) was used for removing odour from ice boxes, the solution being applied to a sponge, which was used to wipe the interior of the ice boxes.

EXAMPLE 6

To Basic Formulations A, B and C of Example 3 were added in each case 2% of PEG (polyethylene glycol). The formulations A, B and C were tested against the equivalents A' B' and C' including 2% of PEG by applying a standard amount of each to a respective garbage can containing restaurant waste standing outdoors in average ambient temperature of 25° C.

Each garbage can so treated was left for 48 hours and the relative odour levels eminating from the treated and untreated garbage cans were qualitatively assessed.

In the result the odour levels of cans treated with A' B' and C' were found to be significantly lower after 48 hours than the garbage cans treated with compositions A, B and C. Nevertheless a garbage can left absolutely free of compositions in accordance with the present invention had a very high odour level indeed.

EXAMPLE 7

The compositions A, B and C of Example 3 were tested in accordance with the following protocol by "Schweizeriche Institute Fur Hauswirtschaft (S.I.H.)" (Swiss Institute for Home Economics).

5 drums were tested. Each drum contained a piece of carpet which had been subjected to prolonged exposure to abattoir waste to saturate it with a strong organic smell. 3 of the drums were then sprayed respectively with compositions A, B and C, one drum being left unsprayed while the last drum was treated with a conventional odour masking agent.

Subsequently 20 liters of air were pumped twice for 30 minutes from a drum into a bag whereupon the air in the bag was qualitatively assessed by a panel.

The results were as follows:
Sample 1 Untreated;
odour concentration 1216
Total hydrocarbon value 2 ppm Sample 2 Conventional;
odour control product
odour concentration 1050
Total hydrocarbon value 2.5 ppm
Sample 3 Composition A
odour concentration 385
Total hydrocarbon value 2.9 ppm
Sample 4 Composition B
odour concentration 529
Total hydrocarbon value 2.9 ppm
Sample 5 Composition C
Odour concentration 239
Total hydrocarbon value 2.0 ppm Thus sample 5 showed the best effect with an odour reduction of about 80%.

I claim:

1. An odour removal composition comprising
   (a) a complexing agent which is a biguanide polymer of the formula (1)

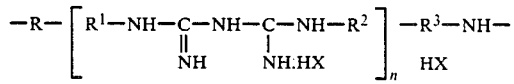

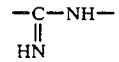

in which R, $R^1$, $R^2$ and $R^3$ are a substituted or unsubstituted alkylene group having up to 12 carbon atoms in the unsubstituted chain, HX is an acid, and n has a value of 2 to 20;
   (b) a carrier capable of assisting wetting of odour forming compositions; and
   (c) a cationic moiety; said moiety being part of a chemically independent compound, or chemically associated with a complexing agent or the carrier.

2. A composition according to claim 1 characterised in that R to $R^3$ have 1 to 5 carbon atoms, HX is inorganic and wherein n has a value of 5 to 15.

3. A composition according to claim 1 wherein R to $R^3$ have the formula $-(CH_2)-_Y$ wherein Y is 3 and wherein n has a value of 3 to 10.

4. A composition according to claim 1 characterised by the inclusion of a minor amount of a substantially odourless aromatic ester of low volatility.

5. A composition according to claim 1 characterised by the presence of a quaternary ammonium salt and/or an organic acid, and/or a betain compound.

6. A composition according to claim 5 characterised in that the quaternary ammonium salt is aromatic and/or the organic acid is selected from citric, ascorbic or lactic acids.

7. A composition according to claim 5 characterised in that the quaternary ammonium compound is dimathylbenzyl ammonium chloride, the complexing agent is the reaction product of citric, ascorbic or lactic acid and a reacrive salt of iron or copper and in that the carrier is a non-ionic or amphoteric surfactant.

8. A composition according to claim 1 comprising 20 to 80% by volume of a quaternary ammonium compound, 5 to 40% by volume of the polymer of formula (1) and up to 75% by volume of the carrier composition.

9. A composition according to claim 1 characterised by the inclusion of a buffering agent to provide a pH of 5.5 to 10, and/or a cationic or non-ionic wetting agent.

10. A composition according to claim 1 characterised by containing an enzyme adapte to degrade odour emitting compounds.

11. A composition according to claim 1 characterised in that at least one of the active components is present as an acid or salt of low solubility in aqueous media.

12. An absorbany article impregnated with a composition according to claim 1.

13. A composition according to claim 2 wherein R to $R^3$ have the formula $-(CH_2)-y$ wherein Y is 3 and wherein n has a value of 3 to 10.

14. A composition according to claim 12 wherein HX is sulphuric or hydrochloric acid.

15. A composition according to claim 2 wherein HX is sulphuric or hydrochloric acid.

* * * * *